United States Patent
Wang

(10) Patent No.: US 12,191,026 B2
(45) Date of Patent: Jan. 7, 2025

(54) METHOD FOR CONTROLLING FLAT PANEL DETECTOR, AND UPPER COMPUTER, FLAT PANEL DETECTOR AND MEDICAL SYSTEM

(71) Applicant: BOE Technology Group Co., Ltd., Beijing (CN)

(72) Inventor: Yixiu Wang, Beijing (CN)

(73) Assignee: BOE Technology Group Co., Ltd., Beijing (CN)

(*) Notice: Subject to any disclaimer, the term of this patent is extended or adjusted under 35 U.S.C. 154(b) by 175 days.

(21) Appl. No.: 17/419,264

(22) PCT Filed: Dec. 29, 2020

(86) PCT No.: PCT/CN2020/141001
§ 371 (c)(1),
(2) Date: Jun. 28, 2021

(87) PCT Pub. No.: WO2021/174981
PCT Pub. Date: Sep. 10, 2021

(65) Prior Publication Data
US 2023/0070305 A1    Mar. 9, 2023

(30) Foreign Application Priority Data
Mar. 2, 2020 (CN) .................. 202010134726.X

(51) Int. Cl.
*G16H 30/20* (2018.01)
*A61B 6/46* (2024.01)

(52) U.S. Cl.
CPC ............. *G16H 30/20* (2018.01); *A61B 6/461* (2013.01)

(58) Field of Classification Search
CPC ................................ A61B 6/461; G16H 30/20
See application file for complete search history.

(56) References Cited

U.S. PATENT DOCUMENTS

| 10,117,631 B2* | 11/2018 | Inoue .................. A61B 6/5205 |
| 2005/0020898 A1 | 1/2005 | Vosniak et al. |
| 2010/0044573 A1* | 2/2010 | Yagi ...................... A61B 6/4411 250/370.15 |

(Continued)

FOREIGN PATENT DOCUMENTS

| CN | 106254040 A | 12/2016 |
| CN | 106308828 A | 1/2017 |

(Continued)

*Primary Examiner* — Elias Desta
(74) *Attorney, Agent, or Firm* — IPro, PLLC

(57) ABSTRACT

Disclosed are a method for controlling a flat panel detector, and an upper computer, a flat panel detector and a medical system, so as to solve the problem that a device containing a flat panel detector in the related art has the risk of irradiating a patient with mistakenly used rays in the using process. The method includes: generating and sending a control command to a flat panel detector in response to an operation instruction of a user (101); receiving actual response identification information sent by the flat panel detector when the flat panel detector determines that the control command is a first type of control command (102); and verifying the consistency of the actual response identification information and pre-stored expected response identification information, and generating prompt information (103).

10 Claims, 9 Drawing Sheets

(56) References Cited

U.S. PATENT DOCUMENTS

2013/0046594 A1* 2/2013 Davidson .............. G06Q 30/02
705/14.4

FOREIGN PATENT DOCUMENTS

| CN | 109602432 A | 4/2019 |
| --- | --- | --- |
| CN | 111358483 A | 7/2020 |
| WO | 2012176645 A1 | 12/2012 |

* cited by examiner d# METHOD FOR CONTROLLING FLAT PANEL DETECTOR, AND UPPER COMPUTER, FLAT PANEL DETECTOR AND MEDICAL SYSTEM The present disclosure is a US National Stage of International Application No. PCT/CN2020/141001, filed on Dec. 29, 2020, which claims priority of the Chinese Patent Application No. 202010134726.X, filed to the Chinese Patent Office on Mar. 2, 2020, of which the entire contents are incorporated herein by reference.

FIELD

The disclosure relates to the field of semiconductors, in particular to a method for controlling a flat panel detector, and an upper computer, a flat panel detector and a medical system.

BACKGROUND

The flat panel detector is a core component in an X-ray medical device such as a computed tomography (CT), a direct digital radiography (DR) and a C-shaped arm. The flat panel detector is in communication connection with an upper computer system in two modes, namely wireless connection and wired connection, where the wireless connection uses a wireless network of a hospital, and most of the wired connection uses network cables. In the using process, an upper computer needs to modify and control the exposure parameters, the exposure mode, the working state and the like of the flat panel detector, but the risk that signals are interfered exists no matter through wireless communication or wired communication, especially under the condition that the electromagnetic environment such as an operating room is complex. If the flat panel detector does not work according to the requirement of the upper computer, the risk that the patient suffers from useless ray exposure exists.

SUMMARY

The disclosure provides a method for controlling a flat panel detector, and an upper computer, a flat panel detector and a medical system, so as to solve the problem in the related art that a device including a flat panel detector has the risk of irradiating a patient with mistakenly used rays in the using process.

The embodiments of the disclosure provide a method for controlling a flat panel detector, and the method includes: generating and sending a control command to the flat panel detector in response to an operation instruction of a user; receiving actual response identification information sent by the flat panel detector when the flat panel detector determines that the control command is a first type of control command; and verifying the consistency of the actual response identification information and pre-stored expected response identification information, and generating prompt information.

In a possible implementation mode, when the control command is generated and sent to the flat panel detector, the method further includes: generating the expected response identification information corresponding to the control command when it is determined that the control command is the first type of control command; and storing the expected response identification information to an expected event queue.

In a possible implementation mode, the determining the control command to be the first type of control command includes: judging whether the control command includes a first type of flag, and when it is determined that the control command includes the first type of lag, determining that the control command is the first type of control command.

In a possible implementation mode, the verifying the consistency of the actual response identification information and pre-stored expected response identification information includes: reading the actual response identification information sequentially from a receive event queue, where the receive event queue is used for storing the actual response identification information fed back by the flat panel detector; controlling a count value to be increased by one when it is determined that the read actual response identification information is the same as one of the expected response identification information; and judging whether a numerical value of the count value is the same as the number of the expected response identification information in an expected event queue or not.

In a possible implementation mode, the generating the prompt information includes: generating parameter setting success prompt information when it is determined that the actual response identification information is consistent with the expected response identification information; and generating parameter setting failure prompt information and failure reason prompt information when it is determined that the actual response identification information is inconsistent with the expected response identification information.

In a possible implementation mode, the receiving actual response identification information sent by the flat panel detector when the flat panel detector determines that the control command is a first type of control command includes: entering a receiving thread when it is determined that the control command is the first type of control command; judging whether the buffer is empty or not cyclically for multiple times; extracting a feedback control command sent by the flat panel detector from a buffer when it is determined that the buffer is not empty in the current judgment process, where the feedback control command includes a corresponding flag and the actual response identification information; and adding the actual response identification information in the feedback control command into the receive event queue when it is determined that the corresponding flag in the feedback control command is a first type of flag.

In a possible implementation mode, the receiving actual response identification information sent by the flat panel detector when the flat panel detector determines that the control command is a first type of control command further includes: ending the receiving thread when it is determined that the buffer is empty in the current judgment process.

In a possible implementation mode, after receiving actual response identification information sent by the flat panel detector when the flat panel detector determines that the control command is a first type of control command and before verifying the consistency of the actual response identification information and pre-stored expected response identification information and generating prompt information, the control method further includes: judging whether the quantity of the received actual response identification information is not less than the quantity of the expected response identification information or not.

The embodiments of the disclosure further provide a method for controlling a flat panel detector, and the method includes: receiving a control command sent by an upper computer; and sending a feedback control command including actual response identification information to the upper computer when it is determined that the control command is a first type of control command.

In a possible implementation mode, the sending a feedback control command including actual response identification information to the upper computer when it is determined that the control command is a first type of control command includes: judging whether the control command includes a first type of flag or not, and in response to determining that the control command includes the first type of flag, determining that the control command is the first type of control command; generating a feedback control command including the corresponding flag and the actual response identification information; and sending the feedback control command to the upper computer.

The embodiments of the disclosure provide an upper computer, including a first processing component used for executing the method provided by the embodiments of the disclosure.

The embodiments of the disclosure further provide a flat panel detector, including a second processing component used for executing the method provided by the embodiments of the disclosure.

The embodiments of the disclosure further provide a medical system, including the upper computer provided by the embodiments of the disclosure and the flat panel detector provided by the embodiments of the disclosure.

The embodiments of the present disclosure have the beneficial effects that: the method for controlling the flat panel detector provided by the embodiments of the disclosure includes: generating and sending a control command to the flat panel detector in response to an operation instruction of a user; receiving actual response identification information sent by the flat panel detector when the flat panel detector determines that the control command is a first type of control command; and verifying the consistency of the actual response identification information and the pre-stored expected response identification information, and generating prompt information, that is, important commands can be set as first-type control commands, after the upper computer sends the relatively important first-type control commands, the flat panel detector needs to carry out corresponding feedback, and if the upper computer determines that an actual response identifier fed back by the flat panel detector is inconsistent with the expected response identification information pre-stored in the upper computer, a prompt can be given to the user, so that the user can perform corresponding adjustment for avoiding misoperation, and therefore, the control commands are divided into a response-needing type and a response-free type according to the importance of the control commands, a response-free control command is quickly sent for setting unimportant parameters of the flat panel detector; and for a response-needing control command, closed-loop control is formed by sending the control command, receiving feedback and verifying responses, and is used for setting important parameters of the flat panel detector, so that the real-time performance and stability of device operation are ensured, invalid exposure caused by signal interference or detector errors and the like is reduced, and the risk problem that a patient is irradiated by mistakenly used rays is avoided.

DETAILED DESCRIPTION OF THE EMBODIMENTS

In order to make the purpose, the technical solution and the advantages of the embodiment of the present disclosure clearer, the technical solution of the embodiments of the present disclosure will be clearly and completely described in combination with accompanying drawings of the embodiments of the present disclosure. Obviously, the described embodiments are a part of the embodiments of the present disclosure, but not all the embodiments of the present disclosure. Based on the described embodiments of the present disclosure, all other embodiments obtained by those of ordinary skill in the art without creative labor belong to the scope of protection of the present disclosure.

Unless additionally defined, the technical or scientific terms used by the present disclosure should be of general meaning understood by persons with general skills within the field to which the present disclosure belongs. The "first", "second", and similar words used in the present disclosure do not represent any order, quantity, or importance, but are only used to distinguish different components. Similar words such as "including" or "containing" meaning that elements or objects appearing in front of the word encompass elements or objects listed behind the word and their equivalents, without excluding other elements or objects. Similar words such as "connection" or "connected" are not limited to physical or mechanical connection, but may include electrical connection, either direct or indirect. The "upper", "lower", "left", "right" and the like are only used for representing the relative position relation, and when the absolute position of the described object is changed, the relative position relation can also be correspondingly changed.

In order to keep the following description of the embodiments of the present disclosure clear and simple, the present disclosure omits detailed description of known functions and known components.

In a traditional X-ray medical device system using a flat panel detector, open-loop control is mostly adopted, that is, after an upper computer sends a control command, feedback of the flat panel detector is not judged, instead, the overall communication stability is improved simply by increasing the sending frequency of important commands; and some devices are subjected to simple closed-loop control, but only whether the flat panel detector receives the command is judged, but whether parameters or states are modified according to requirements of the command after the detector receives the command is not judged, so that although the risk that the signal is interfered is reduced, if the flat panel detector fails and thus does not work according to the requirement of the upper computer, the risk that the doctor and the patient are exposed by useless rays still exists, therefore the embodiments of the present disclosure provide a control method of a flat panel detector, and the control method is described on the upper computer side.

Figure 1:
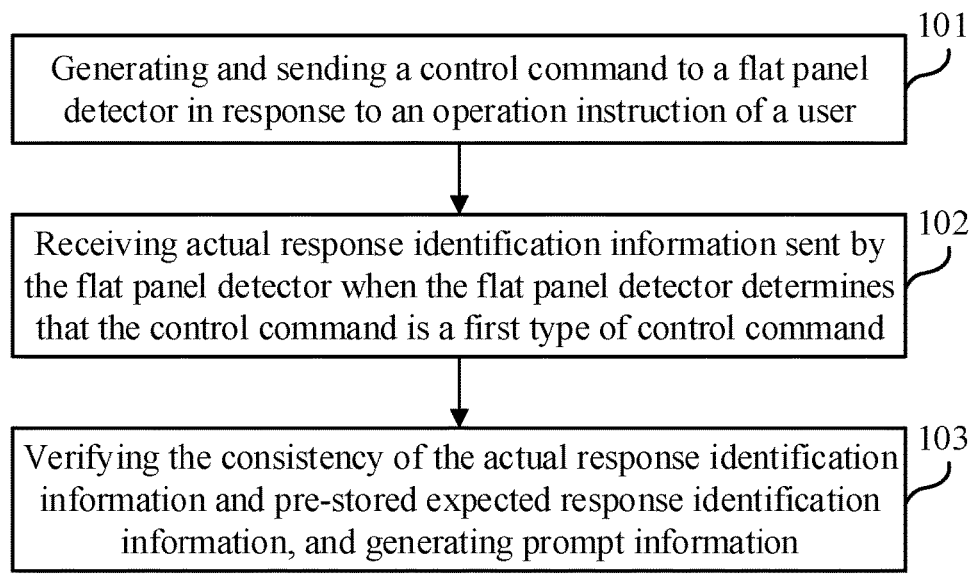
FIG. 1 is a flow chart of a method for controlling a flat panel detector at an upper computer side provided by the embodiments of the disclosure.

As shown in FIG. 1, the embodiments of the present disclosure provide a method for controlling a flat panel detector, including the following operations.

Operation 101, generating and sending a control command to the flat panel detector in response to an operation instruction of a user. Specifically, an upper computer sends the control command to the flat panel detector, where the control command may be a first type of control command that is relatively important and needs to be responded or a second type of control command that is not important and needs not to be responded. A specific operation of the user may be, for example, clicking by the user on a specific sending icon in a display interface associated with the upper computer, and certainly, may also be other operations for sending a control command according to instructions.

Operation 102, receiving actual response identification information sent by the flat panel detector when the flat panel detector determines that the control command is a first type of control command. That is, when the flat panel detector receives the control command, the flat panel detector first judges whether the control command is the first type of control command or not; when the flat panel detector determines the control command is the first type of control command, the flat panel detector returns actual response identification information to the upper computer, and when the flat panel detector determines the control command is not the first type of control command, the flat panel detector may not feed back any information to the upper computer.

Operation 103, verifying the consistency of the actual response identification information and pre-stored expected response identification information, and generating prompt information.

The method for controlling the flat panel detector provided by the embodiments of the present disclosure includes: generating and sending a control command to the flat panel detector in response to an operation instruction of a user; receiving actual response identification information sent by the flat panel detector when the flat panel detector determines that the control command is a first type of control command; and verifying the consistency of the actual response identification information and the pre-stored expected response identification information, and generating prompt information, that is, important commands can be set as first-type control commands, after the upper computer sends the relatively important first-type control commands, the flat panel detector needs to carry out corresponding feedback, and if the upper computer determines that an actual response identifier fed back by the flat panel detector is inconsistent with expected response identification information pre-stored in the upper computer, a prompt can be given to the user, so that the user can perform corresponding adjustment for avoiding misoperation, and therefore, the control commands are divided into a response-needing type and a response-free type according to the importance of the control commands, a response-free control command is quickly sent for setting unimportant parameters of the flat panel detector; and for a response-needing control command, closed-loop control is formed by sending and receiving feedback and response verification, and is used for setting important parameters of the flat panel detector, so that the real-time performance and stability of device operation are ensured, invalid exposure caused by signal interference or detector errors and the like is reduced, and the risk problem that a patient is irradiated by mistakenly used rays is avoided.

In specific implementation, when the operation 101 is executed, that is, when the control command is generated and sent to the flat panel detector, the method further includes the following operations.

Figure 2A:
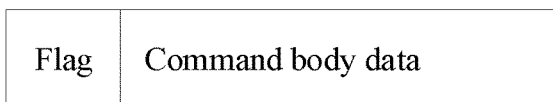
FIG. 2A is a format schematic diagram of a control command provided by the embodiments of the disclosure.
Figure 2B:
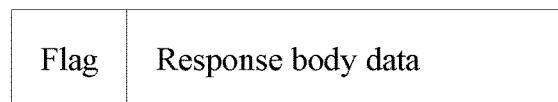
FIG. 2B is a format schematic diagram of a feedback control command provided by the embodiments of the disclosure.

Operation 1011, generating expected response identification information corresponding to the control command when it is determined that the control command is the first type of control command. Specifically, whether the control command is the first type of control command can be determined by judging whether the control command includes a first type of flag, and when it is determined that the control command includes the first type of flag, the control command is determined to be the first type of control command. Namely, for example, the control command may be a data packet composed of a flag and command body data, for a first type of control command that is important and needs to be responded, the flag may be set to be a first type of flag (for example, the flag is set to 1) so as to judge whether the control command is the first type of control command, and for control command that needs not to be responded, the flag may be set to be 0. Specifically, one byte may be allocated to store a flag, the flag value is stored at the front end of the command body data, as shown in FIG. 2A, the flag and the command body data form final control command sending data, similarly, when a receiving end (the flat panel detector) replies a response, the same data format is adopted, as shown in FIG. 2B, the flag and response body data form final feedback control command data received by the upper computer side. Particularly, the data length of the command data and the data length of the response data should be fixed values, so that data extraction is facilitated.

Operation 1012, storing the expected response identification information to an expected event queue. The expected response identification information specifically may be expected response IDs. Specifically, before the upper computer sends the control command to the flat panel detector, an initialization process needs to be completed first, and an expected event queue and a receive event queue need to be created, where the expected event queue is used for storing expected response IDs of the current control command, and the receive event queue is used for storing all actual response IDs received by a receiving thread; and afterwards, the upper computer packs command data to be sent according to a communication protocol, sequentially adds N expected response IDs expected by the flat panel detector for the control command into the expected event queue, and then empties the receive event queue. After the expected event queue and the receive event queue are created, a control command including flag and command body data is sent to the flat panel detector, if the control command does not need to check the response, the sending is ended, true is returned, and setting success is displayed in a status bar; and if the command needs to judge the response, the current thread is suspended and a receiving thread is entered.

In the embodiments of the present disclosure, when the control command is generated and sent to the flat panel detector, if the control command is the first type of control command, the corresponding expected response identification information is generated and stored in the expected event queue, so that the expected response identification information is subsequently compared with the received actual response identification information, and if the expected response identification information is consistent with the received actual response identification information, it can be determined that the control command received by the flat panel detector is the control command sent by the upper computer.

Figure 3:
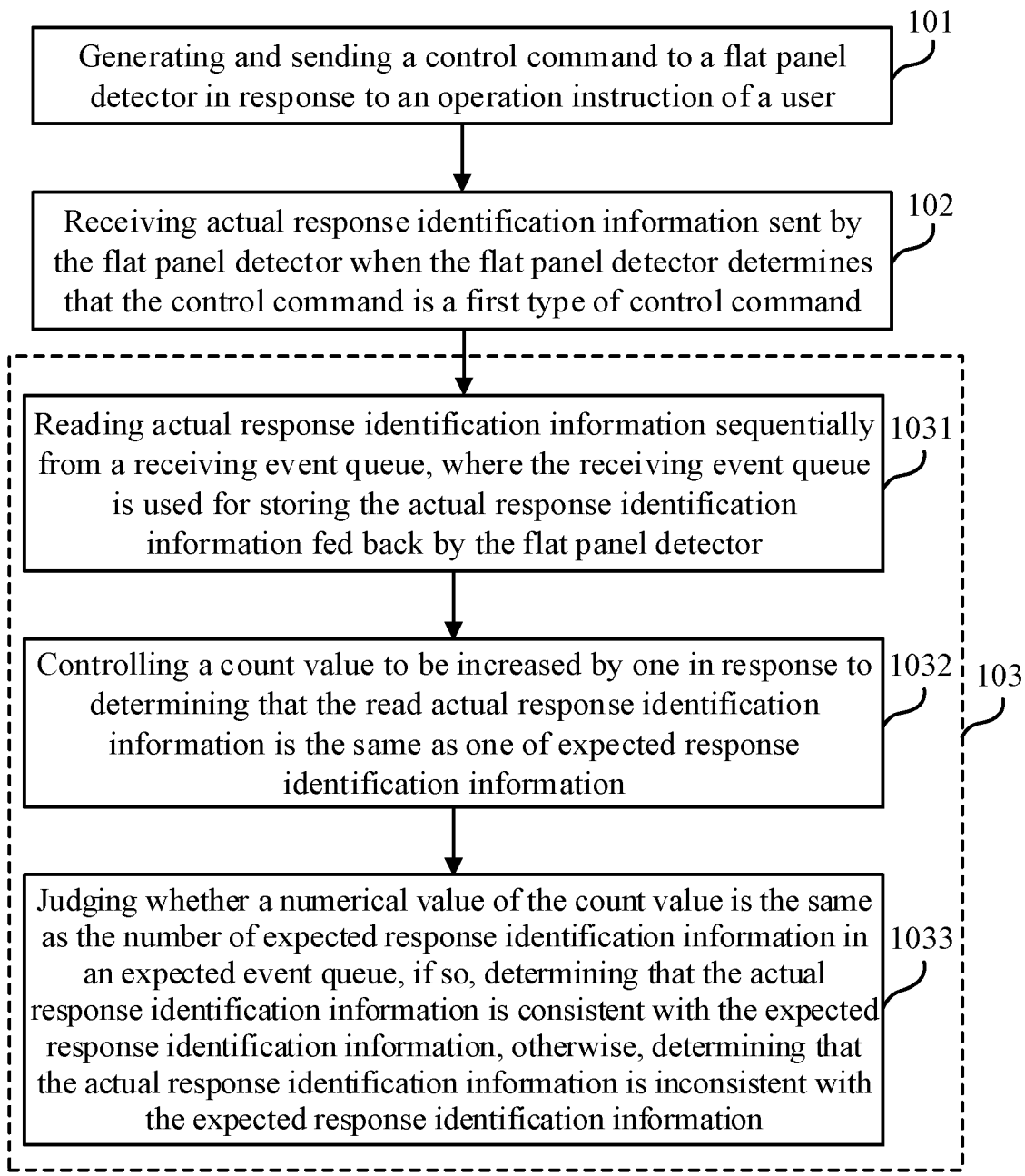
FIG. 3 is a flow chart of a specific method for controlling a flat panel detector at an upper computer side provided by the embodiments of the present disclosure.

In specific implementation, in combination with FIG. 3, verifying the consistency of the actual response identification information and pre-stored expected response identification information in step 103 includes the following operations.

Operation 1031, reading actual response identification information sequentially from the receive event queue, where the receive event queue is used for storing the actual response identification information fed back by the flat panel detector. That is, while the expected event queue is created, the receive event queue is created so as to be used for storing the actual response identification information received subsequently. The actual response identification information specifically may be a plurality of actual response IDs.

Operation 1032, controlling the count value to be increased by one when it is determined that the read actual response identification information is the same as one of the expected response identification information. That is, whether the read actual response ID is one of IDs in the expected event queue is verified, when it is determined that the read actual response ID is one of IDs in the expected event queue, the count value is increased by 1, and when it is determined that the read actual response ID is not any one of IDs in the expected event queue, the next step 1033 is directly executed.

Operation 1033, judging whether the numerical value of the count value is the same as the number of the expected response identification information in the expected event queue or not.

In specific implementation, the generating the prompt information in operation 103 includes the following operations.

Figure 4A:
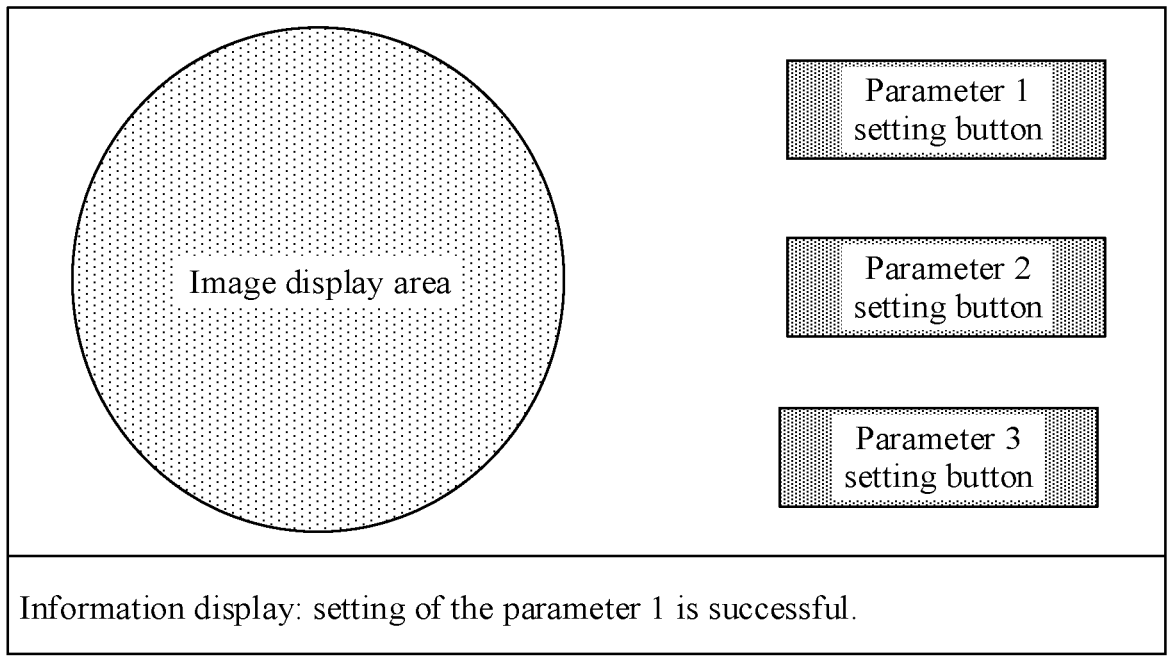
FIG. 4A is a schematic diagram of a display interface provided by the embodiments of the disclosure.

Operation 1034, generating parameter setting success prompt information when it is determined that the actual response identification information is consistent with the expected response identification information. Namely, if the count value is the same as the number of expected response IDs in the expected event queue, it is determined that the actual response identification information is consistent with the expected response identification information, then the verification thread is ended, and parameter setting success prompt information is generated. Specifically, the generated parameter setting success prompt information can be displayed through a display interface, as shown in FIG. 4A, the display interface may include an image display area, a parameter 1 setting button, a parameter 2 setting button and a parameter 3 setting button, and when actual response identification information generated during setting of a parameter 1 is consistent with expected response identification information, prompt information "setting of the parameter 1 is successful" can be displayed at the lower part of the display interface.

Figure 4B:
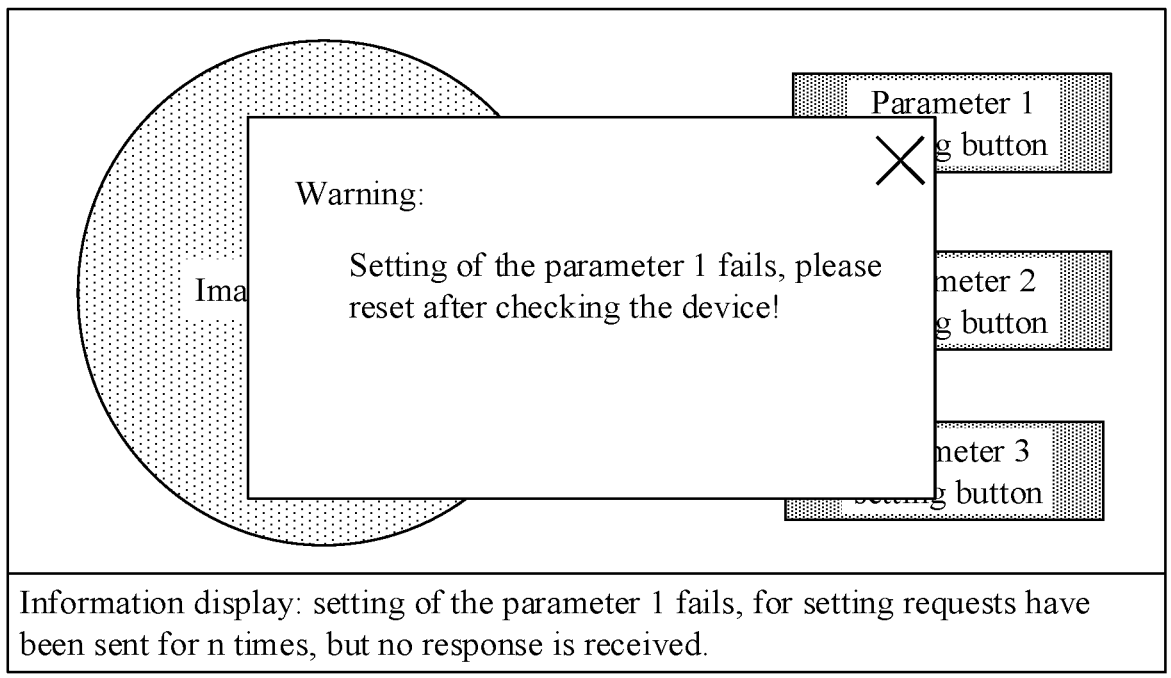
FIG. 4B is a schematic diagram of another display interface provided by the embodiments of the disclosure.

Operation 1035, generating parameter setting failure prompt information and failure reason prompt information when it is determined that the actual response identification information is inconsistent with the expected response identification information. Specifically, if the count value is different from the number of expected response IDs in the expected event queue, the method returns to the step 1031, and statistical judgment is carried out again. Specifically, before returning to the step 1031 each time, whether the verification thread is timed out or not can be judged for one time, if the verification thread is timed out, it is indicated that expected N actual response IDs are not received within the specified time, false is returned, the verification thread is ended, and parameter setting failure prompt information and failure reason prompt information are generated; and if the verification thread is not timed out, the flow of the statistical judgment of this time is entered. Specifically, the display of generated parameter setting failure prompts and resending of prompt information can be realized through a display interface, as shown in FIG. 4B, the display interface may include an image display area, a parameter 1 setting button, a parameter 2 setting button and a parameter 3 setting button, and when actual response identification information generated during setting of a parameter 1 is inconsistent with expected response identification information, prompt information "information prompt: setting of the parameter 1 fails, for setting requests have been sent for n times, but no response is received" can be displayed at the lower part of the display interface, and prompt information "setting of the parameter 1 fails, please reset after detecting the device!" is displayed through a pop-up box.

In the embodiments of the disclosure, through interface design, whether parameter setting is successful or not is displayed in the interface in real time, and if the parameter setting fails, possible error reasons are analyzed and prompted, so that a user can conveniently find problems. Therefore, while the stability of device operation is improved, invalid exposure caused by signal interference or detector errors and the like is reduced, and extra ray radiation to doctors and patients is avoided, a user is enabled to know fairly well through a friendly interface design, so that the next operation is facilitated, and meanwhile, the real-time performance of the whole communication control system is also considered.

Figure 5:
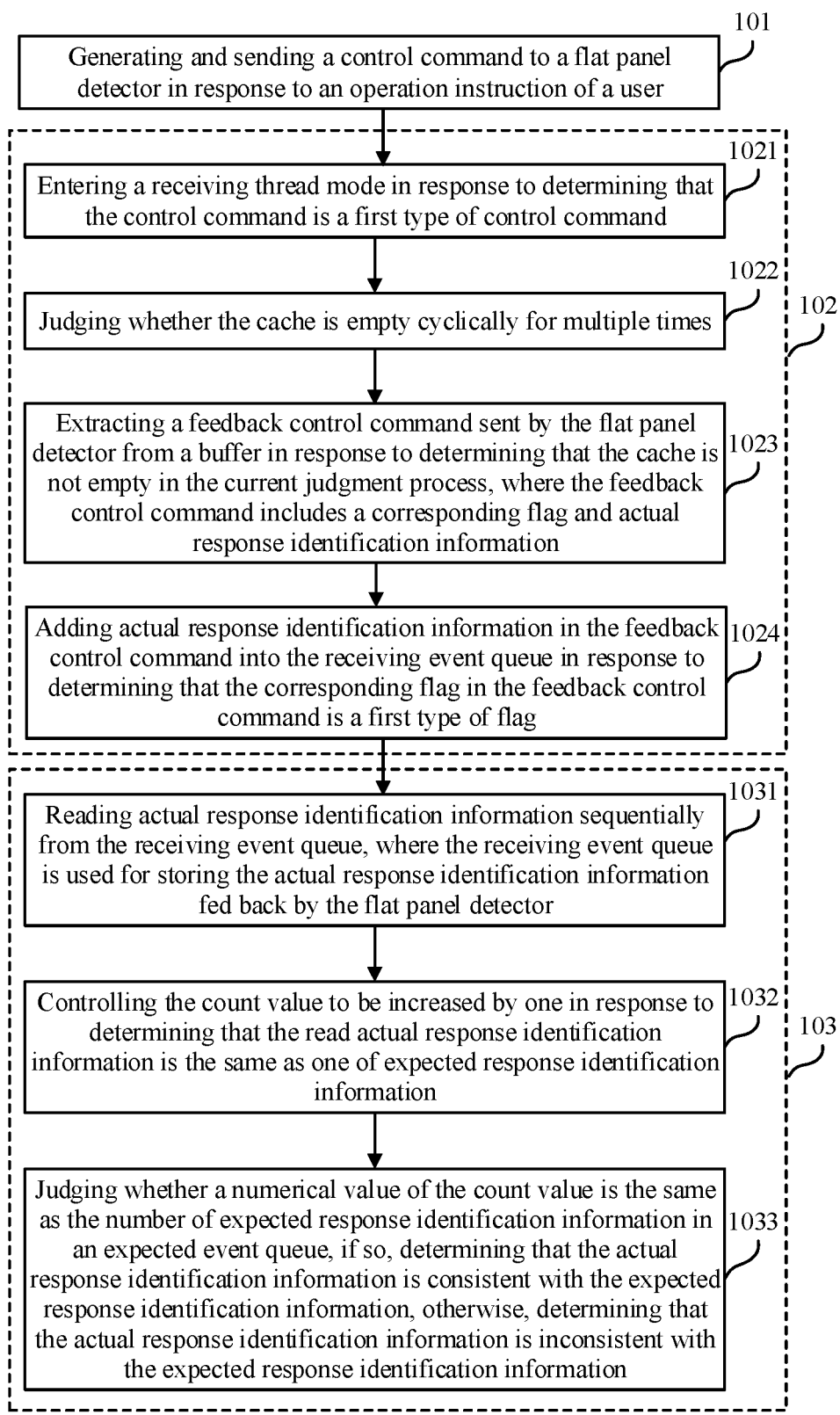
FIG. 5 is a flow chart of another specific method for controlling a flat panel detector at an upper computer side provided by the embodiments of the disclosure.

In specific implementation, as shown in FIG. 5, receiving actual response identification information sent by the flat panel detector when the flat panel detector determines that the control command is the first type of control command in the operation 102 includes the following operations.

Operation 1021, entering a receiving thread when it is determined that the sent control command is the first type of control command. Specifically, after the receiving thread is entered, a mutual exclusion variable 1 can be locked firstly to prevent simultaneous running of the verification thread and the receiving thread.

Operation 1022, judging whether the buffer is empty or not cyclically for multiple times. That is, the receive buffer is read to judge whether the buffer is empty or not, if the buffer is empty, it is indicated that no response has been received at present, this receiving is ended, the mutual exclusion variable 1 is unlocked, and the next receiving is waited.

Operation 1023, extracting a feedback control command sent by the flat panel detector from the buffer when it is determined that the buffer is not empty in the current judgment process, where the feedback control command includes a corresponding flag and actual response identification information. That is, if the buffer is not empty, it is indicated that the response is received, and a piece of response data is extracted.

Operation 1024, adding actual response identification information in the feedback control command into the receive event queue when it is determined that the corresponding flag in the feedback control command is a first type of flag. That is, the flag data of the first byte of the feedback control command is read, if the flag is 0, it is indicated that the flag data is not response data, the step 1022 is executed again to judge whether the buffer is empty or not to continue to extract the next piece of data; if the flag is 1, it is indicated that the data is a response, then a response ID in the data is added into the receive event queue, the step 1022 is continued to be executed to judge whether the buffer is empty or not, and the steps are repeated in this way until all the data in the receive buffer are extracted, this receiving thread is ended, and the mutual exclusion variable 1 is unlocked.

In specific implementation, receiving actual response identification information sent by the flat panel detector when the flat panel detector determines that the control command is a first type of control command in operation 102 further includes the following operations.

Operation 1025, ending the receiving thread when it is determined that the buffer is empty in the current judgment process. That is, if the buffer is empty in the current judgment process, the receiving thread is ended, and the operation 103 can be executed to enter the related steps of the verification thread.

In specific implementation, between the operation 102 and the operation 103, i.e. after receiving actual response identification information sent by the flat panel detector when the flat panel detector determines that the control command is a first type of control command, and before verifying the consistency of the actual response identification information and pre-stored expected response identification information and generating prompt information, the control method further includes: operation 104, judging whether the quantity of the received actual response identification information is not less than the quantity of the expected response identification information or not. That is, the verification thread is executed only when it is determined that the quantity of the actual response IDs is not less than the number of the expected response IDs, so that the verification success rate can be improved, and the execution time of the whole control method is reduced.

Figure 6:
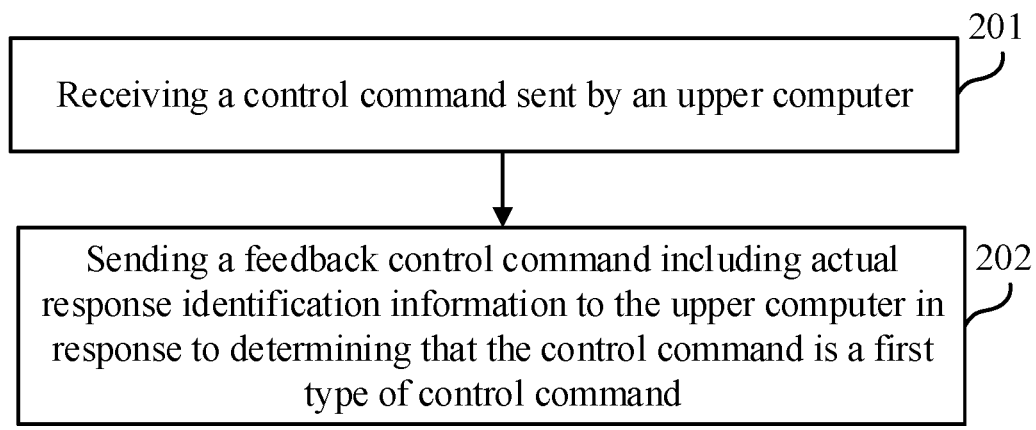
FIG. 6 is a flow chart of a method for controlling a flat panel detector side provided by the embodiments of the disclosure.

Based on the same inventive concept, the embodiments of the disclosure further provide a method for controlling a flat panel detector, as shown in FIG. 6, the method includes the following operations.

Operation 201, receiving a control command sent by an upper computer.

Operation 202, sending a feedback control command including actual response identification information to the upper computer when it is determined that the control command is a first type of control command.

In the embodiments of the disclosure, after the flat panel detector side receives the control command sent by the upper computer, if it is determined that the control command is a first type of control command, the feedback control command including the actual response identification information is fed back to the upper computer, namely, feedback is made to the relatively important control command sent by the upper computer, therefore, the upper computer side knows whether the flat panel detector receives the control command or not and whether the control command received by the flat panel detector is the control command sent by the upper computer or not so as to correctly execute subsequent operations.

In specific implementation, sending a feedback control command including actual response identification information to the upper computer when it is determined that the control command is a first type of control command in step 202 includes the following operations.

Operation 2021, judging whether the control command includes a first type of flag or not, and when it is determined that the control command includes the first type of flag, determining that the control command is the first type of control command. That is, specifically, the flat panel detector side can determine whether the control command is a first type of control command by judging whether the control command includes the first type of flag.

Operation 2022, generating a feedback control command including a corresponding flag and actual response identification information.

Operation 2023, sending the feedback control command to the upper computer.

Based on the same inventive concept, the embodiments of the disclosure provide an upper computer, including a first processing component used for executing the method provided by the embodiments of the disclosure.

Based on the same inventive concept, the embodiments of the disclosure further provide a flat panel detector, including a second processing component used for executing the method provided by the embodiments of the disclosure.

Based on the same inventive concept, the embodiments of the disclosure further provide a medical system, including the upper computer provided by the embodiments of the disclosure and the flat panel detector provided by the embodiments of the disclosure.

In order to more clearly understand the method for controlling the flat panel detector provided by the embodiments of the disclosure, further detailed description is carried out in combination with the following drawings shown in FIG. 7-FIG. 10.

Figure 7:
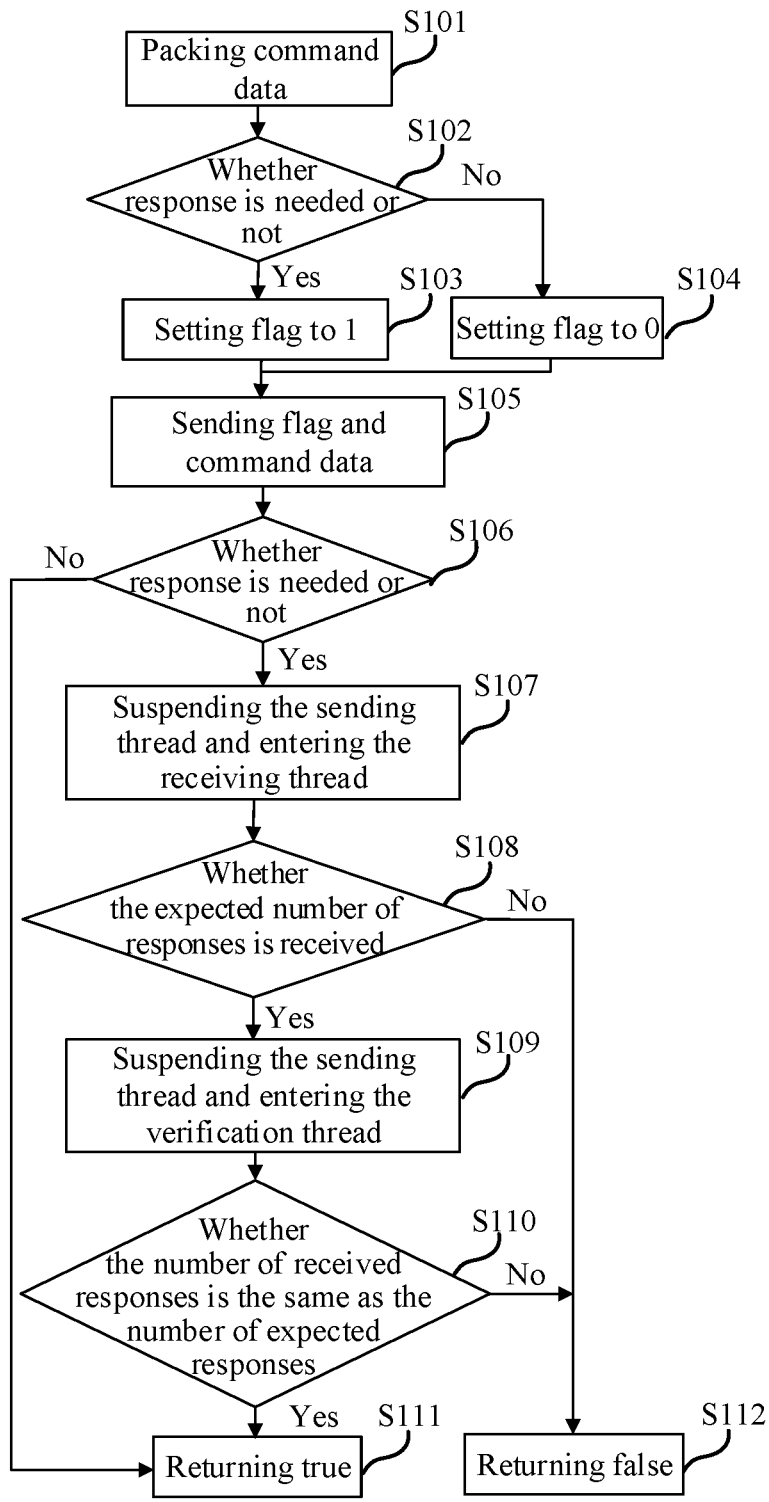
FIG. 7 is a flow chart of a specific integral control method provided by the embodiments of the disclosure.

As shown in FIG. 7 which is a flow chart of an overall control method provided by the embodiments of the disclosure, and the control method includes S101 to S112.

S101, packing data of a control command according to a communication protocol of a flat panel detector.

S102, judging whether the control command is an important response-needing control command or not. When it is determined that the control command is the important response-needing control command, S103 is executed, and when it is determined that the control command is not the important response-needing control command, S104 is executed.

S103, setting a flag of the control command to be 1.

S104, setting the flag of the control command to be 0. Furthermore, the flat panel detector can determine whether response needs to be made by judging the flag after receiving the control command.

S105, sending a control command data packet including the flag and command body data.

S106, judging whether the control command needs to be responded or not. When it is determined that the control command needs to be responded, S107 is executed, and when it is determined that the control command does not need to be responded, S111 is executed.

S107, suspending a sending thread, and entering a receiving thread.

S108, judging whether the flat panel detector receives an expected number of responses or not. When it is determined that the flat panel detector receives the expected number of responses, S109 is executed, and when it is determined that the flat panel detector does not receive the expected number of responses, S112 is executed.

S109, suspending the sending thread, and entering a verification thread.

S110, judging whether the number of the received actual response IDs is the same as the number of the expected response IDs or not. If the number of the received actual response IDs is the same as the number of the expected response IDs, S111 is executed, and if the number of the received actual response IDs is different from the number of the expected response IDs, S112 is executed.

S111, returning true, and displaying parameter setting success prompt information on the user interface.

S112, returning false, and displaying parameter setting failure prompt information and failure reason prompt information on the user interface. That is, if the flat panel detector really works according to the state required by the upper computer, returning true; and otherwise, returning false. Thus, one-time complete important parameter setting of the flat panel detector is completed by sending a command, receiving feedback and verifying responses, closed-loop control is formed, and a user knows the current state of the detector through interface design.

Figure 8:
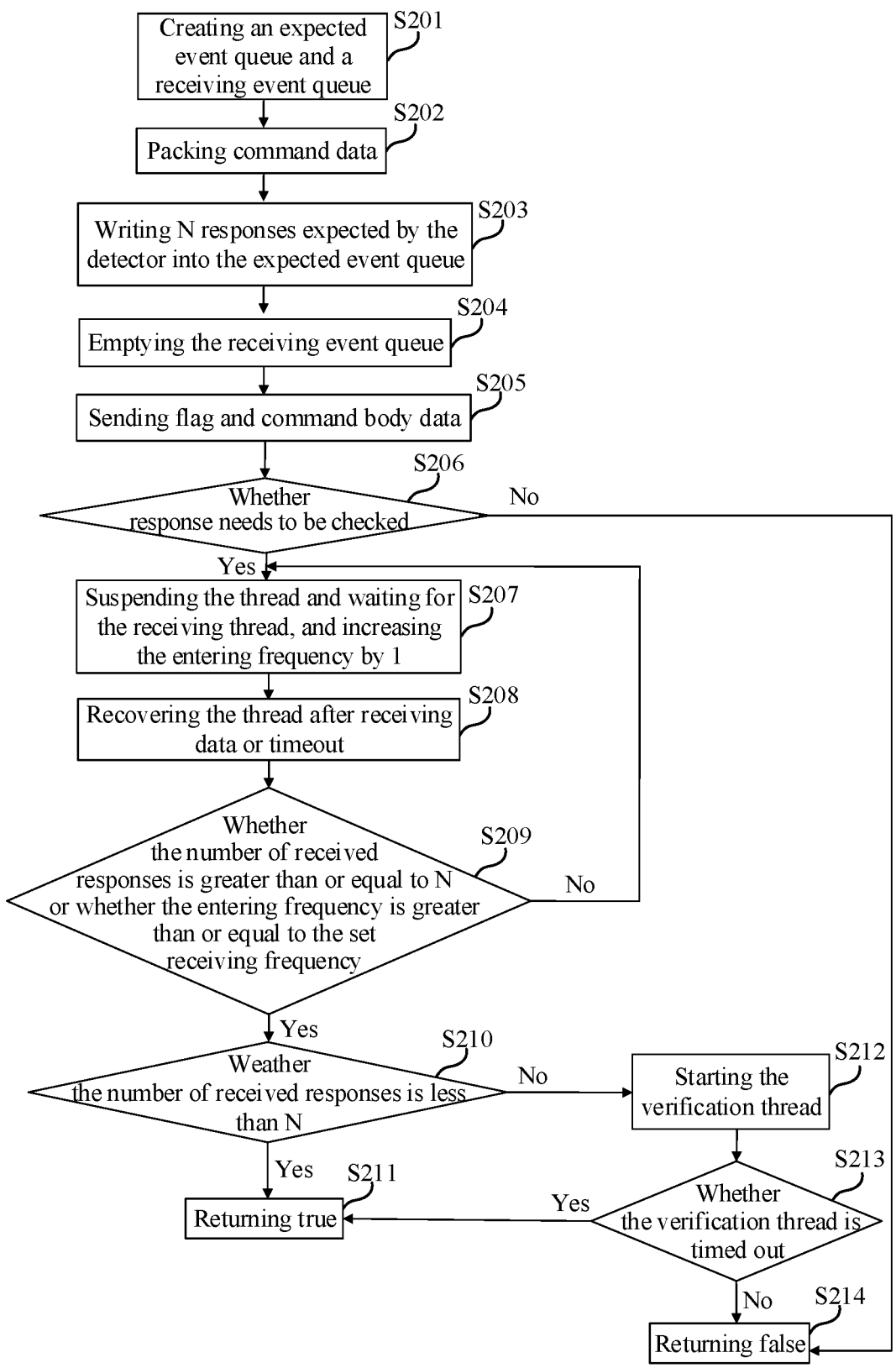
FIG. 8 is a flow chart of a control method mainly based on a sending thread provided by the embodiments of the disclosure.

As shown in FIG. 8 which is a flow chart of a control method mainly based on a sending thread, and the control method includes S201 to S214.

S201, creating an expected event queue and a receive event queue, where the expected event queue is used for storing expected response IDs of the current control command, and the receive event queue is used for storing all response IDs received by the receiving thread. That is, before the upper computer sends a control command to the flat panel detector, initialization work can be completed firstly.

S202, packing the command data to be sent according to a communication protocol.

S203, adding N expected response IDs of the flat panel detector to the command into the expected event queue in sequence.

S204, emptying the receive event queue.

S205, sending a control command including flag and command body data to the flat panel detector.

S206, judging whether the control command needs to be responded or not. If the control command needs to be responded, S207 is executed, and if the control command does not need to be responded, S214 is executed.

S207, suspending the current thread, entering a receiving thread, and recording that the receiving frequency try is increased by 1. Namely, the process is prevented from entering an endless loop by recording the receiving frequency try and returning false when the receiving frequency try reaches the set receiving frequency times, and displaying parameter setting failure prompt information and failure reason prompt information on the user interface.

S208, recovering the receiving thread after receiving the data or timeout.

S209, judging whether the number of received response IDs is greater than or equal to N or the receiving frequency try is greater than or equal to the set receiving frequency times, if so, executing S210, otherwise, executing S212, where N is specifically the number of expected response IDs.

S210, judging whether the number of received actual response IDs is less than N, if yes, executing S211, and if no, executing S212.

S211, returning false.

S212, starting a verification thread S212.

S213, judging whether the verification thread is timed out, if yes, executing S211, and if no, executing S214.

S214, returning true.

After the sending thread is suspended and the receiving thread is entered each time, the receiving frequency try is increased by 1, and when the receiving thread reads response data (feedback control command) or waits for timeout, the sending thread is recovered, the operation is repeated for multiple times in this way until the number of the received actual response IDs reaches the expected N or the receiving frequency try exceeds the preset receiving frequency, the cycle is ended, and false is returned. After the sending thread is recovered, judgment is made firstly, if N responses are not received after try times of receiving, indicating that communication errors exist or the flat panel detector fails, false is returned, a message box pops up to prompt a user that parameter setting fails, and possible error reasons are displayed in a status bar at the lower part; and if at least N actual response IDs are received, a verification thread is started, the current thread is suspended, and a verification result is waited.

Figure 9:
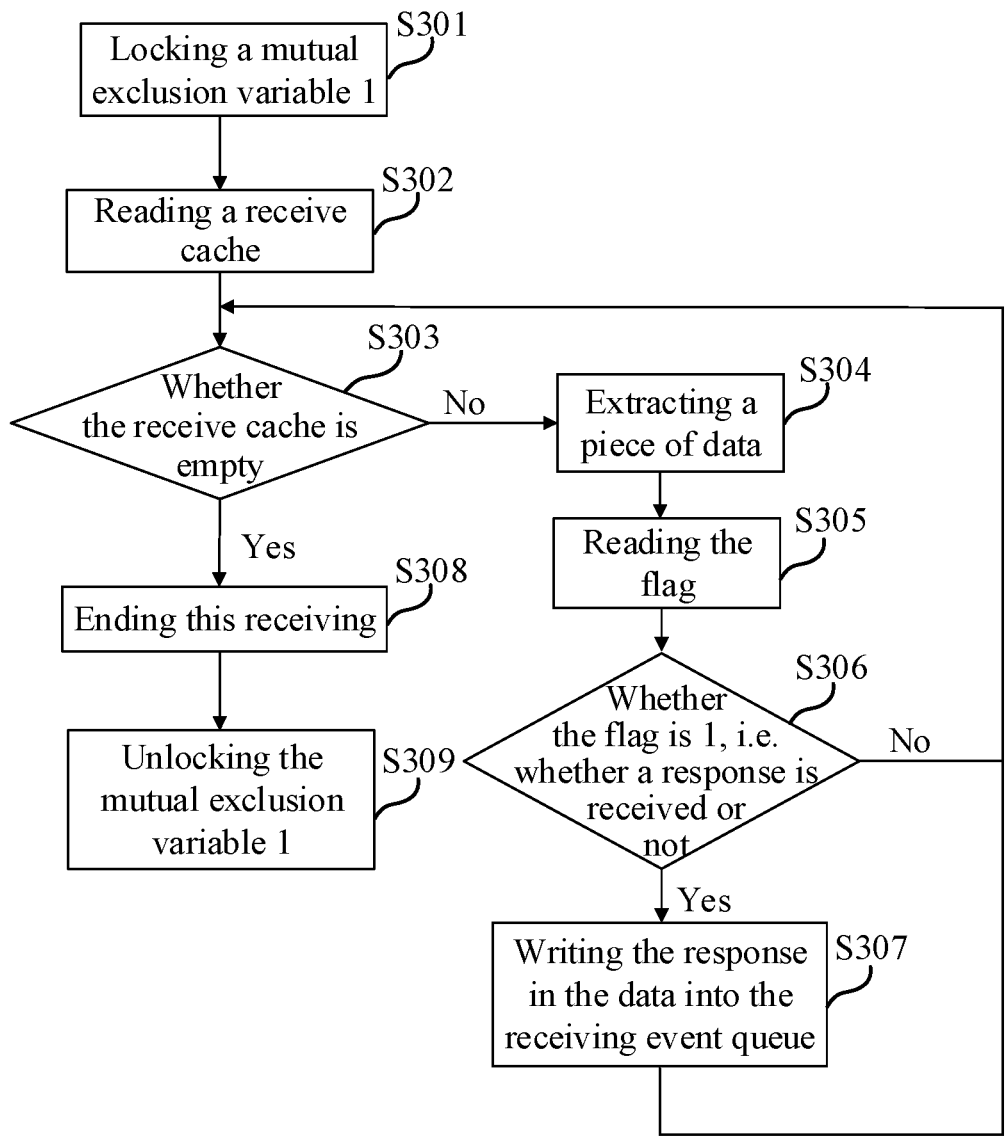
FIG. 9 is a flow chart of a control method mainly based on a receiving thread provided by the embodiments of the disclosure.

As shown in FIG. 9, which is a flow chart of a control method mainly based on a receiving thread, and the control method includes S301 to S309.

S301, locking a mutual exclusion variable 1. In other words, after the receiving thread is entered, the mutual exclusion variable 1 is locked firstly to prevent simultaneous running of the verification thread and the receiving thread, after the mutual exclusion variable 1 is locked, the receiving thread is temporarily suspended, after this verification is finished, the mutual exclusion variable 1 is unlocked, and the receiving thread is recovered.

S302, reading a receive buffer.

S303, judging whether the buffer is empty or not, if yes, executing S308, and if no, executing S304.

S304, extracting a piece of data (feedback control command). That is, the buffer may specifically store a receive event queue, in which a feedback control command may be placed.

S305, reading flag data of the first byte in the piece of data (feedback control command).

S306, judging whether the flag is 1 or not, if yes, executing S307, and if no, executing S303.

S307, adding a response ID in the data into the receive event queue, and continuing to judge whether the buffer is empty or not. The above steps are repeated in this way until all data in the receive buffer are extracted.

S308, ending this receiving.

S309, unlocking the mutual exclusion variable 1.

Figure 10:
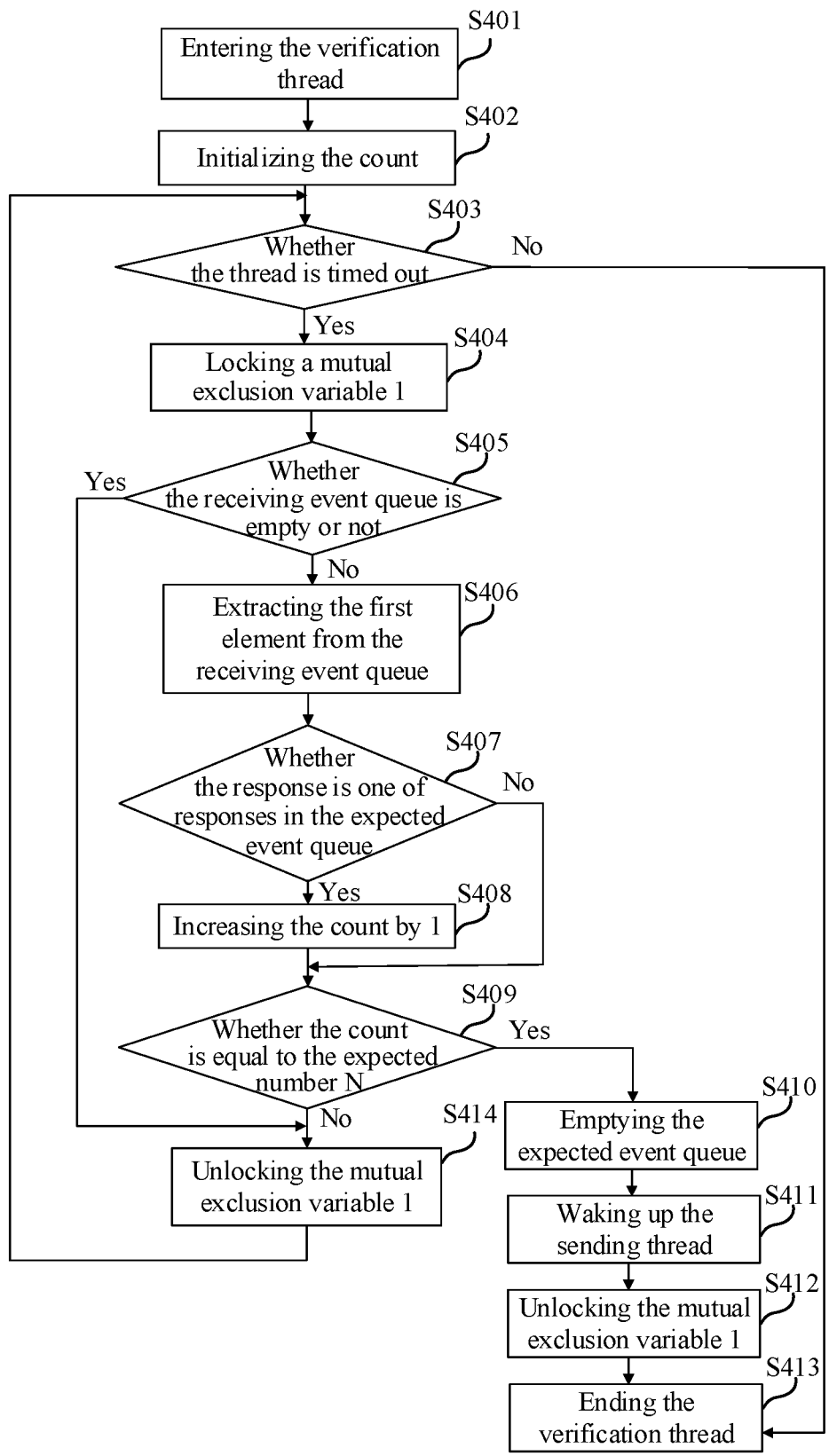
FIG. 10 is a flow chart of a control method mainly based on a verification thread provided by the embodiments of the disclosure.

As shown in FIG. 10 which is a flow chart of a control method mainly based on a verification thread, and the control method includes S401 to S414.

S401, entering a verification thread.

S402, initializing the count to be equal to 0. In order to count the number of responses meeting the expected responses in all the received responses, the count is initialized to be 0 every time the verification thread is entered.

S403, judging whether the verification thread is timed out or not, if yes, executing S403, and if no, executing S413.

S404, locking a mutual exclusion variable 1, where the mutual exclusion variable is used for avoiding simultaneous running of the verification thread and the receiving thread, the receiving thread is temporarily suspended after the mutual exclusion variable 1 is locked, and after this verification is finished, the mutual exclusion variable 1 is unlocked, and the receiving thread is recovered.

S405, judging whether the receive event queue is empty or not, if yes, executing S414, if no, executing S406, and if the receive event queue is empty, it is indicated that no response has been received at present, then the mutual exclusion variable 1 is unlocked, and the receiving thread is recovered to continue to receive data; and if the receive event queue is not empty, it is indicated that the response is received, and then verification is started.

S406, taking out the first element (i.e., an actual response ID in the feedback control command) from the receive event queue.

S407, judging whether the actual response ID is one of response IDs in the expected event queue, if so, executing S408 and increasing the count by 1, otherwise, keeping the count unchanged, and if no, executing S409.

S408, increasing the count by 1.

S409, judging whether the count value is equal to the number N of response IDs in the expected event queue, if so, executing S410, and if no, executing S414.

S410, emptying the expected event queue.

S411, waking up the sending thread.

S412, unlocking the mutual exclusion variable 1.

S413, ending the verification thread.

S414, unlocking the mutual exclusion variable 1, performing thread timeout judgment again, and repeating the above steps to continue to judge the next data in the expected event queue until the thread is timed out or all expected responses are received.

If the verification thread is timed out, it is indicated that N expected response IDs are not received within the specified time, false is returned, a message box pops up to prompt a user that parameter setting fails, and possible error reasons are displayed in a status bar; if the sending thread is waken up within the specified time, it is indicated that all expected response IDs are received, then sending is ended, the verification thread is ended, true is returned, and parameter setting success is displayed in the status bar at the lower part.

The embodiments of the present disclosure have the beneficial effects that the control method of the flat panel detector provided by the embodiment of the disclosure includes: generating and sending a control command to the flat panel detector in response to an operation instruction of a user; receiving actual response identification information sent by the flat panel detector when the flat panel detector determines that the control command is a first type of control command; and verifying the consistency of the actual response identification information and the pre-stored expected response identification information, and generating prompt information, that is, important commands can be set as first-type control commands, after the upper computer sends the relatively important first-type control commands, the flat panel detector needs to carry out corresponding feedback, and if the upper computer determines that an actual response identifier fed back by the flat panel detector is inconsistent with the expected response identification information pre-stored in the upper computer, a prompt can be given to the user, so that the user can perform corresponding adjustment for avoiding misoperation, and therefore, the control commands are divided into a response-needing type and a response-free type according to the importance of the control commands, a response-free control command is quickly sent for setting unimportant parameters of the flat panel detector; and for a response-needing control command, closed-loop control is formed by sending the control command, receiving feedback and verifying responses, and is used for setting important parameters of the flat panel detector, so that the real-time performance and stability of device operation are ensured, invalid exposure caused by signal interference or detector errors and the like is reduced, and the risk problem that a patient is irradiated by mistakenly used rays is avoided.

Obviously, those skilled in the art can make various modifications and variants to the disclosure without departing from the spirit and scope of the disclosure. In this way, if these modifications and variants of the disclosure belong to the scope of the claims of the disclosure and their equivalent technologies, the disclosure is also intended to contain these modifications and variants.

What is claimed is:

1. A method for controlling a flat panel detector, comprising:
generating a control command in response to an operation instruction of a user;
generating an expected response identification information corresponding to the control command in response to determining that the control command is a first type of control command;
storing the expected response identification information to an expected event queue;
sending the control command to the flat panel detector;
receiving actual response identification information sent by the flat panel detector when the flat panel detector determines that the control command is the first type of control command; and
verifying consistency of the actual response identification information and the expected response identification information, and generating prompt information.

2. The method according to claim 1, wherein the determining the control command to be the first type of control command comprises:
judging whether the control command comprises a first type of flag, and in response to determining that the control command comprises the first type of flag, determining that the control command is the first type of control command.

3. The method according to claim 1, wherein the verifying the consistency of the actual response identification information and the expected response identification information comprises:
reading the actual response identification information sequentially from a receive event queue, wherein the receive event queue is used for storing the actual response identification information fed back by the flat panel detector;
controlling a count value to be increased by one in response to determining that the read actual response identification information is the same as one of the expected response identification information; and
judging whether a numerical value of the count value is the same as a quantity of the expected response identification information in the expected event queue or not.

4. The method according to claim 3, wherein the generating the prompt information comprises:
generating parameter setting success prompt information in response to determining that the actual response identification information is consistent with the expected response identification information; and generating parameter setting failure information and failure reason prompt information in response to determining that the actual response identification information is inconsistent with the expected response identification information.

5. The method according to claim 1, wherein the receiving the actual response identification information sent by the flat panel detector when the flat panel detector determines that the control command is the first type of control command comprises:

entering a receiving thread in response to determining that the control command is the first type of control command;

judging whether a buffer is empty or not cyclically for multiple times;

extracting a feedback control command sent by the flat panel detector from the buffer in response to determining that the buffer is not empty in the current judgment process, wherein the feedback control command comprises a corresponding flag and the actual response identification information; and adding the actual response identification information in the feedback control command into a receive event queue in response to determining that the corresponding flag in the feedback control command is a first type of flag.

6. The method according to claim 5, wherein the receiving the actual response identification information sent by the flat panel detector when the flat panel detector determines that the control command is the first type of control command further comprises:

ending the receiving thread in response to determining that the buffer is empty in the current judgment process.

7. The method according to claim 1, wherein after the receiving the actual response identification information sent by the flat panel detector when the flat panel detector determines that the control command is the first type of control command and before the verifying the consistency of the actual response identification information and the expected response identification information, the method further comprises:

judging whether a quantity of the received actual response identification information is not less than a quantity of the expected response identification information or not.

8. A method for controlling a flat panel detector, comprising:

receiving a control command sent by an upper computer; and judging whether the control command comprises a first type of flag or not, and in response to determining that the control command comprises the first type of flag, determining that the control command is a first type of control command;

generating a feedback control command comprising a corresponding flag and actual response identification information; and sending the feedback control command to the upper computer.

9. A flat panel detector, comprising a second processing component, wherein the second processing component is used for executing the method according to claim 8.

10. An upper computer, comprising a first processing component, wherein the first processing component is used for executing:

generating a control command in response to an operation instruction of a user;

generating an expected response identification information corresponding to the control command in response to determining that the control command is a first type of control command;

storing the expected response identification information to an expected event queue;

sending the control command to the flat panel detector;

receiving actual response identification information sent by the flat panel detector when the flat panel detector determines that the control command is the first type of control command; and verifying consistency of the actual response identification information and the expected response identification information, and generating prompt information.

* * * * *